United States Patent
Sambusseti

(10) Patent No.: US 9,375,306 B2
(45) Date of Patent: Jun. 28, 2016

(54) ABSORBABLE PATCH, IN REINFORCED PGA, FOR THE REPLACEMENT OF A PORTION OF BLADDER WALL FOLLOWING PARTIAL CYSTECTOMY

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 85 days.

(21) Appl. No.: 14/382,574

(22) PCT Filed: Mar. 6, 2013

(86) PCT No.: PCT/EP2013/054540
§ 371 (c)(1),
(2) Date: Sep. 3, 2014

(87) PCT Pub. No.: WO2013/135544
PCT Pub. Date: Sep. 19, 2013

(65) Prior Publication Data
US 2015/0148912 A1    May 28, 2015

(30) Foreign Application Priority Data
Mar. 12, 2012 (IT) .............................. MI2012A0381

(51) Int. Cl.
| | | |
|---|---|---|
| *A61F 2/04* | (2013.01) | |
| *A61F 2/00* | (2006.01) | |
| *A61L 31/06* | (2006.01) | |
| *A61L 31/14* | (2006.01) | |
| *A61B 17/06* | (2006.01) | |
| *A61L 27/26* | (2006.01) | |
| *A61L 27/60* | (2006.01) | |

(52) U.S. Cl.
CPC ............ *A61F 2/042* (2013.01); *A61B 17/06166* (2013.01); *A61F 2/0063* (2013.01); *A61L 27/26* (2013.01); *A61L 27/60* (2013.01); *A61L 31/06* (2013.01); *A61L 31/14* (2013.01); *A61L 31/148* (2013.01); *A61F 2210/0004* (2013.01); *A61F 2230/0006* (2013.01); *A61L 2430/22* (2013.01)

(58) Field of Classification Search
CPC .......... A61F 2/04; A61F 2/042; A61F 2/0063
See application file for complete search history.

(56) References Cited

U.S. PATENT DOCUMENTS

| | | |
|---|---|---|
| 2002/0055786 A1 | 5/2002 | Atala |
| 2005/0113938 A1 | 5/2005 | Jamiolkowski et al. |
| 2005/0283246 A1* | 12/2005 | Cauthen et al. ............ 623/17.16 |

FOREIGN PATENT DOCUMENTS

| | | |
|---|---|---|
| WO | 2011/018300 | 2/2011 |
| WO | 2011/064110 | 6/2011 |
| WO | WO 2011064110 A1 * | 6/2011 |

OTHER PUBLICATIONS

International Search Report dated Mar. 28, 2013, corresponding to PCT/EP2013/054540.

* cited by examiner

*Primary Examiner* — Thomas J Sweet
*Assistant Examiner* — Daniel Bissing
(74) *Attorney, Agent, or Firm* — Young & Thompson

(57) ABSTRACT

A patch (1) for the replacement of a portion of bladder wall, following partial cystectomy, comprises a textile (2) derived from a PGA yarn and provided with a star-shaped support frame, flexible and harmonic, formed by a plurality of radial strips (3) manufactured by injection of a PGA/PLA copolymer, the patch (1) being suitable for making autologous fibrous capsule cells, generated by the process of tissue reconstruction, grow thereon after its insertion inside the patient.

20 Claims, 2 Drawing Sheets

ABSORBABLE PATCH, IN REINFORCED PGA, FOR THE REPLACEMENT OF A PORTION OF BLADDER WALL FOLLOWING PARTIAL CYSTECTOMY

BACKGROUND OF THE INVENTION

1. Field of the Invention

The present invention relates to a reinforced absorbable patch for the replacement of a portion of bladder wall following partial bladder removal (cystectomy).

2. Description of the Related Art

As is known, when a portion of the bladder of a patient is affected by a serious disease, such as partial neoplasm or bilharzia (schistosomiasis), this portion of bladder must be removed to prevent the disease spreading to the entire bladder. The removal of this portion of bladder wall creates a hole in the bladder which is closed by using a patch which is sutured in the perimeter of the bladder wall which defines this hole.

Patches are generally devices made up of tissue deriving from the intestine of the patient turned inside out or from synthetic textiles, for example silicone or textile in polypropylene as described in the patent applications WO 2007/039160 and PCT/EP2008/006352 in the name of the Applicant, rendered more biocompatible by means of covering with a layer of pyrolytic turbostratic carbon, or of fatty acids of the omega-3 family.

The purpose of synthetic patches is to replace temporarily the part of bladder removed while awaiting regeneration of the tissues of the bladder around the hole and therefore they have to be removed at a later time by means of subsequent further surgery endoscopically on a day hospital basis. This operation however is not always easy to carry out, in particular on elderly patients.

Moreover bladder patches have to possess a combination of properties which cannot always be achieved by known synthetic or natural patches: such rigidity as to allow the bladder to retain its shape at least until its removal, and at the same time sufficient elasticity and flexibility as to ensure the correct deformation of the patch during the physiological functioning of the treated bladder.

Additionally the bladder patch has to exhibit both chemical resistance and impermeability to urine at least for the entire period from the implanting up to its removable, or absorption. Moreover the patch must not collapse under the weight of the growing tissues, a phenomenon which is instead typical of low-thickness patches, nor exhibit adherences to the surrounding fibrous capsule.

An alternative solution to the aforementioned patches which are not absorbable is represented by the use of three-dimensional matrices, generally in bioabsorbable material, which act as substrate to be populated with stem cells of the diseased organ grown in vitro in order to obtain a piece of biological tissue which will then be implanted in place of the portion of diseased tissue. This procedure allows excellent results to be obtained in terms of compatibility and mechanical performances but is very complex, with long performance times, and costly.

In order to overcome the aforementioned disadvantages the Applicant has developed an absorbable patch in PGA fibres and reinforced with strips of PGA textile able to overcome the limits of the prior art stated above. See patent application WO2011/064110. However further tests performed by the Applicant have shown that this patch very often tends to collapse towards the interior of the bladder, very probably due to the weight of the neotissue growing after the implant: this collapse leads to uneven growth of the neotissue creating adherences in the point of implant and adherence to the fibrous capsule.

Moreover this patch, being made throughout with fibres of PGA homopolymer, has an absorption time of the order of 30 days, similar to the time of growth of bladder neotissue: this entails a decline in the mechanical properties during this period of absorption which consequently leads to the collapse of said patch under the weight of the new tissue growing, given the decreased rigidity in said space of time.

US 2005/0113938 describes a biocompatible implant for the reconstruction of tissues, different from the bladder tissue, formed by a foam made up, among others, of PGA/PLA which is reinforced with textile elements or meshes, formed, among others, by fibres of PGA/PLA.

This implant is however poorly suitable for the replacement of a bladder wall in light of the high porosity, both of the foam and of the reinforcement elements, which, although on the one hand ensures the populating of the implant by the growing neotissue, on the other hand determines an undesirable leakage of urine from the bladder during the growth of the autologous neotissue.

Moreover both the solutions of the aforementioned prior art have little possibility of adapting and conforming, during surgery, to the portion of bladder removed in the case wherein the latter has a curvature, albeit slight.

BRIEF SUMMARY OF THE INVENTION

The object of the present invention is to eliminate, at least in part, the disadvantages of the prior art, by supplying a specific patch for the replacement of a portion of bladder wall, following partial cystectomy, which does not require a subsequent surgical operation for its removal.

Another object of the present invention is that of providing such a patch which is also practical for the surgeon and at the same time simple and fast to make.

Yet another object of the present invention is to provide such a patch which is reliable, in particular as regards the impermeability and resistance to urine, which does not swell up once implanted and which has good mechanical strength, in particular which does not exhibit collapsibility when cell tissues grow over it, in order to ensure good performances of bladder deformation during its functioning.

A further object of the present invention is to provide such a patch which can moreover be populated by the new biological wall tissue of the portion of bladder removed without having a negative influence on the growth of said tissue, does not adhere to the fibrous capsule and which is reliable without exhibiting possible leaks and/or releases of liquid and is resistant to urine and impermeable thereto.

Yet another object is that of providing such a patch which is elastic/flexible for the correct deformation of the device during the physiological functioning of the bladder, but provided also with an improved rigidity and such as to support the growing neotissue during the time of its absorption such as to allow a homogeneous and even growth of the neotissue.

A further object is moreover that of providing such a patch which also exhibits a high capacity for being shaped during the operation in order to adapt to the shape of the portion of bladder wall removed in case the latter exhibits, during the operation, a curvature, albeit slight.

These objects are achieved in accordance with the invention with the features listed in the claims.

Advantageous embodiments of the invention are disclosed by the dependent claims. The self-supporting patch according to the invention, which is ready for use without any surface cell covering, for the replacement of a portion of bladder wall following partial cystectomy, is made up of absorbable materials (bioabsorbable) and is in the form of textile, supported by a frame with radial arms in the shape of a star.

This patch is suitable for guaranteeing a correct deformation of the bladder whereto it is applied and at the same time a non-collapsibility as the new cell tissues grow.

The internal and external surfaces of said patch are without sowing of cultured cells and in this condition the patch is implanted in the patient, in the absence of any previous covering by cultured tissue cells and any surface treatment suitable for encouraging the grafting of the growing tissues.

In practice the aforesaid patch has been found to be suitable for acting as scaffold after insertion inside the patient, making only autologous fibrous capsule cells grow on it, generated by the process of tissue reconstruction of the patient, which only takes place after its insertion.

The textile is made by using a multifilament or ultra-light-weight monofilament yarn, deriving from fibres of PGA (polyglycolide or polyglycolic acid), preferably homopolymer.

PGA is a biodegradable thermoplastic polymer characterised by a high degree of crystallinity, around 45-55% in the case of the homopolymer. PGA is unstable hydrolytically and, when exposed to physiological conditions, degrades thanks to random hydrolysis processes, but also thanks to some classes of enzymes, more particularly belonging to the family of the esterases. Despite this, this material is particularly suitable for not deteriorating in contact with the urine for a period of at least two months.

PGA also has a time of degradation which ranges from 4 to 6 months, even reaching 12 months, but starts to lose its mechanical strength already after 4 weeks and is completely lost at the fifth month. This however is compatible with the cell growth of the bladder tissues and resistance to urine, not exhibiting any swelling (increase in volume and in dimensions) during this period.

The PGA fibres preferred in order to make the textile of the present patch are those deriving from the homopolymer since they are presented as very rigid and are characterised by a high value of tensile modulus equal to 7 GPa and a minimum tensile strength of at least 4.5 grams/deniers.

Thanks to these properties, the textile obtained with the use of said PGA fibres is found to have a sufficient mechanical consistency while allowing the textile obtained from them to be flexible.

The textile of the absorbable patch of the present invention can be made by weaving in various ways said PGA multifilament or monofilament, creating a knit textile, a woven textile or a nonwoven textile.

It is in any case preferable to use a knit textile, more particularly warp knit, in that provided with a more wrinkled surface compared to the other manufactured types mentioned above.

The use of a textile rather than a foam is advantageous in that it has such impermeability as not to allow the urine to escape from the device during the growth of the neotissue in combination with such porosity as to facilitate the growth of the neotissue.

It is moreover also preferable for the textile of the patch to be texturised. It has in fact been found that texturisation, in addition to making the fabric more wrinkled on the surface, also confers a greater rigidity and impermeability to urine compared to a non-texturised textile. In fact it is believed that the texturisation goes to cover further the micro-holes which exist between the meshes of the textile.

The texturisation of the textile can be performed in various ways: by means of the use of monofilament with wrinkled surface obtained according to the methods known in the art, by means of a heat-setting treatment of the textile in order to obtain raised parts in the fibres, conferring greater volume to the filament. The latter method of texturisation is preferred.

The frame of said textile is substantially planar and formed by a plurality of radial strips, or arms, substantially rigid yet elastic and flexible, which can be slightly curved manually by the surgeon during the operation if necessary. These strips are arranged in such a way as to result in a frame with a star configuration, since said strips extend radially outwards starting from the central point of said frame like the rays or the arms of a star.

Said frame, called as BIOSTAR, was produced on behalf of the Applicant by Mr. Christian Choux.

The frame is obtained by means of injection of a copolymer of glycolic acid and lactic acid, indicated as PGA/PLA (poly (lactic-co-glycolic) acid), and heat forming.

Heat forming is a technique of hot moulding of plastic materials, from sheets or films, under pressure or under vacuum, for example by preheating the sheet or the film of plastic polymer and then laying on the mould this preheated material. Or by pushing the plastic film on the mould thanks to a high pressure exerted from the outside by the air, which also facilitates the cooling thereof. Or by using a mould and counter-mould system actuated mechanically with the aid of hydraulic presses.

This technique enables homogeneous and non-porous elements to be obtained, without holes that are surface and/or inside the bulk of the element, and cannot be used for obtaining fibres of PGA/PLA which are instead formed by using specific methods for the obtaining of fibres such as meltspun, electrospun and the like.

Since lactic acid is a chiral molecule, there are different types of polymer, at times indicated with specific acronyms: PDLA, PLLA, PDLLA, where D and L represent the two stereoisomers. PLLA (poly(L-lactic)acid) has a crystallinity of 37%, a temperature of glass transition between 50 and 80° C., and a melting point of 173-178° C., while the polymer deriving from the polymerisation of a racemic mixture of isomers D and L, PDLLA, is amorphous.

The term poly(lactic) acid, PLA, is intended here to identify all the various types of polymer indicated above.

Once this frame has been obtained, which is found to be more rigid than the textile but at the same time flexible, elastic and harmonic, it is attached onto the surface of the textile in PGA, turned towards the exterior of the bladder, stitching it with suture stitches of absorbable thread, for example with a monofilament in polydioxanone (PDO) with slow absorption such as absorbable MONOTIME®.

Since the textile in PGA and the frame in PGA/PLA are absorbed in approximately 1 month and the time of reformation of the polyprotein capsule is substantially the same, it is clear that the implanted patch does not subsequently have to be removed as it is absorbable substantially with the same rate of growth of the new tissue.

More particularly, the frame in heat-formed PGA/PLA, which exhibits a substantial absorption in the first month (complete after 5-6 months), maintains its rigidity and mechanical properties constant in said first month (which is also the time of growth of the bladder neotissue) thus ensuring the non-collapsibility of the textile in PGA under the weight of the growing bladder neotissue in said space of time.

Moreover during the subsequent 150 days (approximately) after absorption of the textile in PGA, the presence of residual PLA/PGA of the frame during absorption provides an incentive for improvement of the neotissue formed after the first 30 days, since it helps the bladder neotissue to reach in a total of 180 days an optimal profile, consistency, shape and dimension.

The frame therefore has the purpose of supporting the textile which forms the patch for the 30 days necessary for its absorption so as not to make it collapse in order to give to the neotissue a shape and profile identical to the original ones of the portion removed.

BRIEF DESCRIPTION OF THE DRAWINGS

Further features of the invention will be made clearer by the following detailed description referred to its embodiments purely by way of a non-limiting example, illustrated in the accompanying drawings, in which.

DETAILED DESCRIPTION OF THE PREFERRED EMBODIMENTS

The term "patch" here is intended to identify substrates different from those used as scaffolds whereon cultured cells are made to grow, which are implanted in the patient only after having been populated by these cells.

Figure 1:
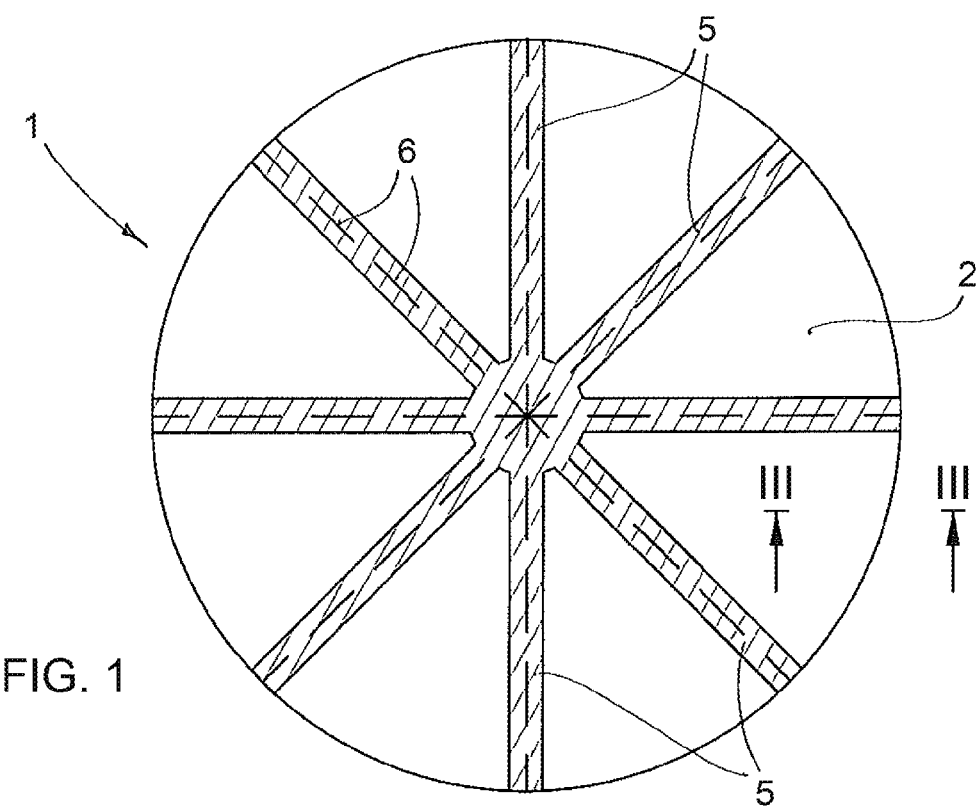
FIG. 1 is a plan view from above of the reinforced patch in accordance with the invention.

In FIG. 1 the patch 1 is represented with a substantially round shape, even if this shape is not binding for the purpose of the present invention. The patch 1 is made up of a fabric 2 deriving from a monofilament or multifilament in PGA, preferably from a multifilament.

When this fabric 2 derives from a monofilament, it is made from a monofilament of PGA having a denier count preferably comprised between 120 and 160 deniers, where the deniers here refer to the diameter of the monofilament. In this case the resulting textile 2 has preferably a denier count (also defined as linear mass density) or grams comprised between 240 and 320 deniers. The term deniers, D, indicates the weight of the textile, where 1 D corresponds to 9,000 meters of yarn with weight 9,000 g (P(g)/L(9,000 m)).

Said patch 1 has the upper 3 and lower 4 surfaces preferably texturised. Upper surface refers to the surface turned towards the exterior of the bladder intended to come into contact with the internal tissues of the patient while lower surface refers to that turned towards the interior of said bladder.

In fact the texturisation improves further the non-adherence of the patch to the fibrous capsule, already moreover good for the textile 2 defined above yet without texturisation. When the fabric 2 of the patch 1 is made with a multifilament yarn of fibres of PGA, this yarn has dimensions of approximately 50-200 deniers.

The textile 2 is preferably made with a 75 deniers/30 filaments (parallel one to the other) yarn, where 75 deniers is the dimension of the yarn corresponding to 75 g/10000 yards of yarn (10000 yards~9000 meters) and 30 is the number of smaller threads which form each yarn.

Moreover said textile 2 is a warp knitted textile: the warp knitting technique is such as not to result in a woven or a nonwoven textile, and not even a felt-like material.

The process of warp knitting is performed on a machine for warp knitting where the yarns are parallel warps and knitted at the same time, with a density preferably of 30 needles/inch.

In this case the weave of the textile 2 is such that the interstitial space is less than 200 microns, preferably around 160 microns, corresponding to an average area of the holes equal to approximately 0.02 mm$^2$. This guarantees impermeability to urine, avoiding leaks.

Preferably the manufacturing pattern of this process of warp knitting is of the type

| | |
|---|---|
| Wales Per Inch (WPI) | 29-30 |
| Courses Per Inch (CPI) | 62-68 |

With this manufacturing pattern and with the preferred yarn indicated above a textile 2 is obtained, having the following features:

| | |
|---|---|
| Average area (mm2) | 0.020 |
| Effective diameter (microns) | 140-180 |
| Porosity | 70-80% |
| Surface density, mg/cm2 | 16-18 |

Figure 2:
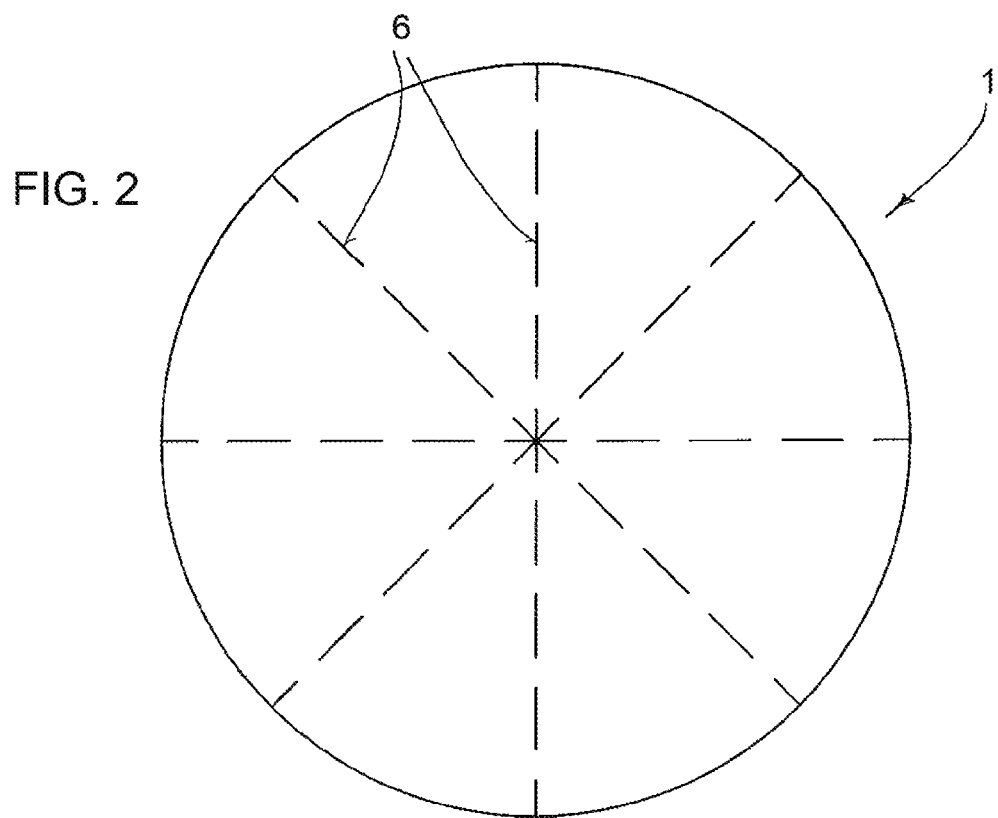
FIG. 2 is a plan view from below of the reinforced patch of FIG. 1.

The upper 3 and lower 4 surfaces (FIG. 2) of the textile 1 appear very wrinkled because they are subjected, preferably, to texturisation, in addition to the warp knit process, in order to increase further the non-adherence to the fibrous capsule.

Generally the thickness of the textile 2 used in the manufacture of the present patch 1 can vary between 0.1 mm and 2 cm. In a preferred embodiment said thickness is approximately 0.3-0.6 mm, more preferably approximately 0.4-0.53 mm, even more preferably 0.45 mm.

The textile 2 preferably has the shape of a circle, with a diameter starting from 3-5 cm, even if it can be made in any shape and dimension, for example with square shape with a side of 200 mm or rectangular shape with dimensions 200 mm×300 mm, 100 mm×200 mm, and can also be formed from a fabric of greater dimensions, for example 10 cm×15 cm.

Said textile 2 is then supported by a frame, with flat or planar structure, formed by a plurality of radial reinforcement strips 5, which detach from the centre of the frame moving outwards, so as to take on a planar stellar configuration.

This frame acts as support, structure for the textile 2, enabling it to maintain a substantially flat or slightly curved shape, also under the weight of the tissue growth, thus obtaining a self-supporting patch.

The PGA/PLA copolymer whereof the frame is constituted and the relative radial strips 5 can be formed, for example, by 30% of PGA and by 70% of PLA.

Particularly preferred as PLA/PGA copolymer (poly (lactic-co-glycolic) acid) is the poly(L-lactic-co-glycolic) copolymer (PLLA/PGA) wherein the L-lactic acid is 82-88% in moles while the glycolic acid is 18-12% in moles. This copolymer is known commercially by the name Resomer® LG 855S.

Generally the thickness of the frame and of the relative strips (arms) can vary between 0.1 and 10 mm, preferably between 0.5 and 2 mm. In a preferred embodiment said thickness is approximately 1 mm.

The frame and the reinforcement strips 5 which are placed on the upper surface 3 of the textile 2 are attached thereto by means of absorbable sutures 6, defining the same number of sectors on the upper surface 3 of the textile 2. Thanks to these sutures 6 it is possible to avoid the use of adhesive materials which could give undesirable reactions.

In a preferred embodiment the total thickness of the patch 1 inclusive of frame and textile 2 is approximately 1.45 mm even if this is not binding for the purpose of the present invention.

The Applicant has surprisingly found that the patch 1 made with a textile 2 in PGA as described above, more particularly texturised, in combination with a heat-formed star-shaped frame in PGA/PLA, exhibits a good mechanical consistency and a sufficient rigidity and flexibility, also in the presence of urine, so that it is able to guarantee a correct deformation of the bladder during the emptying or the filling of the same, exhibiting at the same time a good tightness against leaks of urine.

Moreover the aforesaid textile 2 and also the non-porous frame are found to be neutral when in contact with growing neotissue: this entails a rapid population of the device implanted by the cells of the growing surrounding tissue. At the same time the adhesion was found to be reduced due to the reduced interaction between the polymers which make up the textile and the frame and the biological molecules, thus ensuring a non-fusion with the internal tissues of the patient.

In fact the patch of the present invention has a combination of properties which cannot be found in other known patches, more particularly in that described in WO2011/064110:

- sufficient rigidity, and constant during the arc of growth of the bladder neotissue (approximately 1 month), such as to allow the bladder to maintain its shape until absorption of the patch and, at the same time, not to collapse under the weight of the growing neotissues;
- sufficient elasticity and flexibility such as to ensure the correct deformation of the patch during the physiological functioning of the bladder provided with said patch;
- chemical resistance and impermeability to urine;
- covering by the neotissue, even if not porous;
- non-collapsibility under the weight of the growing tissues;
- non-adherence to the fibrous capsule;
- greater rigidity compared to similar devices intended for the same use yet having reinforcements made in fabric, for example in PGA/PLA;
- greater conformability during the operation thanks to heat-formed reinforcements in harmonic PGA/PLA which can be slightly curved manually by the surgeon, during the operation, if necessary.

Tests performed by the Applicant using similar textile devices with textile reinforcements, made completely in PGA, such as those described in WO2011/064110, have shown that this latter polymer, widely used with success in the medical sector, cannot be used advantageously for the replacement of bladder walls.

More particularly preclinical studies were performed in vivo on a pig bladder implanted with a rectangular patch (with dimensions of approximately 10 cm×15 mm) in monofilament PGA, texturised, having a denier count similar to that of the present textile in PGA of between 50 and 200 deniers, with reinforcement strips taken from the same textile in PGA, in order to evaluate the behaviour of the device in place of a portion of bladder in the time of absorption (1 month) by means of the analysis of the scarring, of the integration of the patch in the tissues, of the functioning of the kidneys, of the lack of local systemic effects. The animal was kept under control by means of laboratory analyses and ultrasound scan starting from the day of the operation of the blood up to the end of the first month (time of absorption of the PGA).

After 14 days it was observed via the ultrasound scan that the device had attached to the walls of the bladder and that the site of the implant exhibited a remodelling with thickening of the bladder wall in its proximity.

The examination at two months from the implant demonstrated adherences of the intestine and of the uterus to the zone of the bladder whereon the patch was implanted, and the presence of zones of dark colour in the scar of the implant zone, indication of the remodelling of the zone.

Moreover the histological examination of this implant zone showed that the scar was formed by mature granulation tissue and incorporated the remaining patch.

These phenomena indicate that the vast portion of bladder removed was not replaced by a new wall of cell tissue of the same dimensions and that the device must have collapsed on itself seeing that it was integrated in the scar tissue. Moreover the composition of the new wall, i.e. of the tissue of the scar, has shown to be mainly mature granulation tissue not covered by urothelium.

Therefore the device in PGA textile reinforced with strips in PGA textile has demonstrated an insufficient mechanical consistency (rigidity), during the duration of the regeneration of the cells of the bladder, since the growing tissue did not go to replace that being absorbed but grew in other directions. The result is a bladder which tends to have an asymmetrical and abnormal shape, different from the original one, therefore potentially irritating for the other surrounding organs.

This is probably due to the fact that the patch in PGA textile with reinforcements in PGA textile has, in general, a lower rigidity which moreover decreases during the time of growth of the neotissue.

On the contrary the present heat-formed frame made in PGA/PLA has shown, despite its absorbability, a sufficient rigidity which moreover has remained constant during the time of growth of the bladder neotissue.

The patch 1 of the invention is prepared in a controlled environment, that is to say with controlled contamination, in a white room. Once manufacture has finished, the patch 1 is placed in a double blister closed with sheet of Tyvek to avoid contaminations, and sent to a cycle of sterilisation with base of EtO (ethylene oxide). At this point the patch is ready to be used in an operation.

Figure 3:
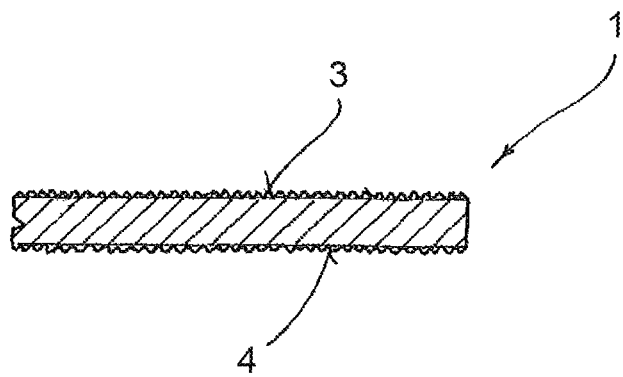
FIG. 3 is an enlarged transverse section view of a portion of patch, wherein the section has been taken along the plane of FIG. 1.
Figure 4:
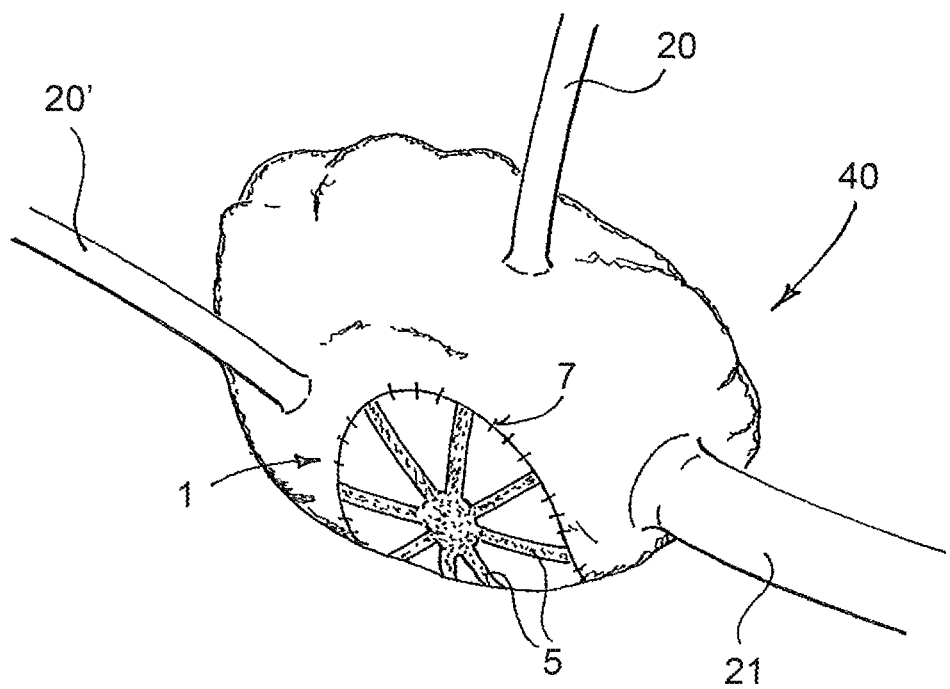
FIG. 4 is a perspective view, illustrating schematically the application to a bladder of the patch according to the invention.

In FIG. 3 a bladder 40 is illustrated schematically with the relative ureters 20, 20' and urethra 21.

In the operation the surgeon removes the zone of the bladder 40 affected by neoplasm and, in order to cover the removal hole, applies a patch 1 by means of suture stitches 7 which connect the perimeter of the patch 1 to the wall of the bladder 40 around the removal hole. Generally the present patch 1 is used when the affected zone does not include the ureters 20, 20' and urethra 21, but is distant from them.

The suture stitches 7 are made with a curved cylindrical needle using a monofilament thread in bioabsorbable (absorbable) material such as that deriving from polymers or copolymers of PGA. The reason for this choice lies in the need for the patch and sutures to be absorbed in the same timespan.

There are however other suture threads in bioabsorbable polymers which could be conveniently adapted to the case in question and to the needs of the patches at the discretion of the surgeon.

The holes of passage of the suture stitches 7 in the bladder 40 do not constitute a risk of leaks of liquid, in that the tissue is reconstructed in a few hours. To avoid leaks of urine (liquid), the holes of the suture stitches 7 can be sealed and closed with a cc (a drop) of surgical glue, such as for example Glubran 2™, normally available commercially.

This glue can also be used optionally on the sutures 6 present on the frame of the textile 2 for the same purpose indicated above, even if this is not necessary.

One of the advantages of the patch of the present invention is that it does not have any risk of adherence to the fibrous capsule in that it is completely absorbable during the regeneration of the zone removed and therefore does not require its removal from the organ wherein they have been implanted by means of subsequent operations.

The use of the patch of the present invention is particularly advantageous in the treatment of localised infections of the bladder such as bilharzia where the removal of the infected part of the bladder is sufficient for guaranteeing the overcoming of the disease, without the need for subsequent treatments or operations.

Moreover this patch can be used also in the treatment of lesions, injury, haematomas, or similar pathologies, of the wall of the bladder following accidents.

Numerous detail modifications and changes, within the reach of a person skilled in the art, may be made to the present embodiments of the invention, in any case coming within the scope of the invention disclosed by the annexed claims.

The invention claimed is:

1. An absorbable self-supporting patch, ready for use without previous cell coverage, for the replacement of a portion of a bladder wall after partial cystectomy and following the covering of said patch by growing autologous fibrous capsule cells generated by a process of tissue reconstruction after the insertion of said patch inside a patient, said patch comprising:
    an absorbable textile made with monofilament or multifilament yarns derived from polyglycolide or polyglycolic acid (PGA) fibers, said textile being supported by a non-porous heat-formed planar frame that is flexible and harmonic, the planar frame being formed by a plurality of heat-formed radial reinforcement strips of poly(lactic-co-glycolic)acid (PGA/PLA) copolymer, said strips extending radially outwards from the center of said frame and being substantially rigid, and elastic and flexible so as to be slightly curved manually by a surgeon during the operation.

2. The patch according to claim 1, wherein the yarn of the textile has a size comprised between 50 and 200 deniers.

3. The patch according to claim 1, wherein the textile is a warp-knitted textile.

4. The patch according to claim 1, wherein the yarn of the textile is a multifilament of the 75 denier/30 filament type.

5. The patch according to claim 1, wherein the textile is a texturized textile.

6. The patch according to claim 1, wherein the profile of the textile is circular.

7. The patch according to claim 1, wherein the thickness of the textile ranges from 0.1 mm to 2 cm.

8. The patch according to claim 1, wherein the radial reinforcement strips which form the frame have a thickness comprised between 0.1 and 10 mm.

9. The patch according to claim 1, wherein the PGA/PLA copolymer of the frame is formed by 30% of PGA and by 70% of PLA.

10. The patch according to claim 1, wherein the PLA/PGA copolymer (poly(lactic-co-glycolic) acid) is a poly(L-lactic-co-glycolic) copolymer (PLLA/PGA), and
    wherein the L-lactic acid is 82-88% in moles while the glycolic acid is 18-12% in moles.

11. The patch according to claim 1, wherein said frame is attached to the textile by absorbable sutures.

12. The patch according to claim 2, wherein the textile is a warp-knitted textile.

13. The patch according to claim 1, wherein the absorbable textile is texturized.

14. The patch according to claim 6, wherein the textile having the circular profile has a diameter comprised between 3 and 5 cm.

15. The patch according to claim 7, wherein the thickness of the textile ranges from 0.3-0.6 mm.

16. The patch according to claim 15, wherein the thickness of the textile ranges from 0.4-0.53 mm.

17. The patch according to claim 16, wherein the thickness of the textile is 0.45 mm.

18. The patch according to claim 8, wherein the radial reinforcement strips which form the frame have the thickness of the radial reinforcement strips comprised between 0.5 and 2 mm.

19. The patch according to claim 18, wherein the radial reinforcement strips which form the frame have the thickness of the radial reinforcement strips comprised of about 1 mm.

20. The patch according to claim 11, wherein the absorbable sutures are monofilament polydioxanone (PDO) with slow absorption.

* * * * *